US006106466A

United States Patent [19]

Sheehan et al.

[11] Patent Number: 6,106,466
[45] Date of Patent: Aug. 22, 2000

[54] AUTOMATED DELINEATION OF HEART CONTOURS FROM IMAGES USING RECONSTRUCTION-BASED MODELING

[75] Inventors: Florence H. Sheehan, Mercer Island; Robert M. Haralick; Paul D. Sampson, both of Seattle, all of Wash.

[73] Assignee: University of Washington, Seattle, Wash.

[21] Appl. No.: 09/066,188

[22] Filed: Apr. 24, 1998

Related U.S. Application Data

[60] Provisional application No. 60/044,791, Apr. 24, 1997.

[51] Int. Cl.$^7$ ........................................................ A61B 8/00
[52] U.S. Cl. ............................................ 600/443; 128/916
[58] Field of Search .................................. 600/443, 447, 600/444, 449; 128/916

[56] References Cited

U.S. PATENT DOCUMENTS

| 5,315,512 | 5/1994 | Roth ........................................ 128/916 |
| 5,435,310 | 7/1995 | Sheehan et al. ........................ 128/916 |

OTHER PUBLICATIONS

T.F. Cootes, A. Hill, C.J. Taylor and J. Haslam, "The Use of Active Shape Models For Locating Structures in Medical Images," *Information Processing In Medical Imaging*, H.H. Barrett and A.F. Gmitro, Eds., Springer–Verlag, Berlin, 1993, pp. 33–47.

Giuseppe Coppini, Riccardo Poli, and Guido Valli, "Recovery of the 3–D Shape of the Left Ventricle from Echocardiographic Images," IEEE Transactions on Medical Imaging, vol. 14, No. 2, Jun. 1995, pp. 301–318.

Edward A. Geiser, MD, Donald A. Conetta, MD, Marian C. Limacher, MD, Vickie Ostlund Stockton, BS, RDMS, Leslie H. Oliver, PhD, and Brian Jones, MD, "A Second–generation Computer–based Edge Detection Algorithm for Short–axis, Two–dimensional Echocardiographic Images: Accuracy and Improvement in Interobserver Variability," Journal of the American Society of Echocardiography, vol. 3, No. 2, Mar.–Apr. 1990, pp. 79–90.

I.L. Herlin and G. Giraudon, "Performing Segmentation of Ultrasound Images using Temporal Information," 1993 IEEE Computer Society Conference on Computer Vision and Pattern Recognition, New York City, New York, Jun. 15–18, 1993, IEEE Computer Society Press, pp. 373–378.

Patrice Lilly, Janice Jenkins, and Patrick Bourdillon, "Automatic Contour Definition on Left Ventriculograms by Image Evidence and a Multiple Template–Based Model," IEEE Transactions on Medical Imaging, vol. 8, No. 2, Jun. 1989, pp. 173–185.

*Primary Examiner*—Jeffrey R. Jastrzab
*Assistant Examiner*—Maulin Podd
*Attorney, Agent, or Firm*—Ronald M. Anderson

[57] ABSTRACT

A method for defining a three-dimensional surface of at least a portion of a patient's heart, based on data obtained by ultrasound imaging of the heart. The imaging is carried out over at least one cardiac cycle and provides a plurality of images in different image planes made with an ultrasound transducer at known positions and orientations. At least three anatomical landmarks in these images are manually identified in each of the images. An ultrasound mesh model in which a three-dimensional abstract mesh defining an archetype shape for a population of other hearts is developed. This abstract mesh has associated with it a covariance that defines the extent of variation of control vertices in the mesh for the population of training data used to derive the mesh model. The mesh model is rigidly aligned with the images of the patient's heart. Predicted images in planes corresponding to those of the images for the patient's heart and derived from the mesh model are compared corresponding images of the patient's heart. Control vertices are included with the abstract mesh for reiteratively adjusting a shape of the mesh model to optimize the fit of the predicted images to the observed images of the patient's heart. This adjustment and comparison continues until an acceptable fit is obtained, yielding an output that defines the shape of the endocardium and epicardium of the left ventricle or other portion of the patient's heart, in three dimensions, for use in determining cardiac parameters.

27 Claims, 10 Drawing Sheets

AUTOMATED DELINEATION OF HEART CONTOURS FROM IMAGES USING RECONSTRUCTION-BASED MODELING

RELATED APPLICATIONS

This application claims priority of U.S. Provisional Patent Application, U.S. Ser. No. 60/044,791, filed on Apr. 24, 1997, the benefit of the filing date of which is hereby claimed under 35 U.S.C. § 119(e).

GOVERNMENT RIGHTS

This invention was made with government support under HL-41464 awarded by the National Institutes of Health, and the government has certain rights to the invention.

FIELD OF THE INVENTION

The present invention generally relates to a method and system for automatically identifying and delineating the boundary or contour of an internal organ from image data, and more specifically, to a method and system for automatically delineating the inner and outer surfaces of the organ by processing image data from multiple planes in three-dimensional space.

BACKGROUND OF THE INVENTION

Disease processes can affect any of the four chambers and four valves of a heart, altering their structure and/or function. Measuring the size, shape, and function of the chambers and valves provides useful information that can assist a physician in evaluating the effect of these disease processes, and of hemodynamic changes, and other influences on the heart. Such measurements may help in diagnosing a patient's health, evaluating the effect of a treatment, assessing prognosis, and understanding the underlying mechanisms of a disease process and its response to therapeutic interventions.

Most commonly, the left ventricle of the heart is investigated. The left ventricle is of greatest importance to health because it pumps blood through most of the body. The right ventricle is also studied, because it provides the impetus for blood circulation through the lungs. One of the most commonly used parameters of heart function is ejection fraction, which indicates the proportion of chamber volume ejected with each heart beat. Other important parameters include ventricular volume, the range of motion of the left ventricular or right ventricular wall, and detection of any thickening of the ventricular wall. These other parameters are generally indicators of regional function, and abnormalities in one or more of the parameters may indicate the presence of coronary artery disease. In addition, the shape of the ventricle provides information regarding its status, because the left ventricle becomes more spherical under certain loading conditions. An evaluation of all of these parameters—volume, shape, ejection fraction, wall motion, and wall thickening—can best be accomplished if the physician has an accurate representation of the ventricular contour.

In clinical practice, these cardiac parameters are generally not measured but rather are estimated visually from two-dimensional images. Methods have been developed to measure these parameters, but such methods typically employ geometrical assumptions concerning the shape of the ventricle. However, these assumptions limit the accuracy of the measurement methods because the heart is a complex organ, and in certain disease states, the geometric assumptions may be invalid. Recent studies have clearly shown that measurement of ventricular volume, mass, and infarct size are more accurate using a three-dimensional approach instead of a two-dimensional analysis. In three-dimensional imaging, the heart is imaged in multiple planes from which the contours of the heart are traced and used to reconstruct the endocardial (inner) and epicardial (outer) ventricular surfaces—without simplifying geometric assumptions. From the three-dimensional reconstruction of the heart, it is also possible to measure the ventricle's shape and parameters of regional function such as wall motion and wall thickening. Variability in measuring parameters of left ventricular size and function by three-dimensional echo is reduced compared to two-dimensional analysis because the latter requires measurements from specific orthogonal views, which cannot be precisely determined. Reducing variability is important to improve diagnostic sensitivity and specificity.

These advantages of quantitative three-dimensional echocardiography have many potential applications, including: diagnostic assessment of patients at rest, analysis of stress studies, pre-operative evaluation, monitoring of cardiac function during cardiac surgery, emergency room assessment of patients with acute chest pain and assessment of non-diagnostic electrocardiograms, evaluation of unstable patients in cardiac or surgical intensive care units, correlation of left ventricular function with perfusion and/or metabolism defects, assessment of prognosis, and quantitative comparison of serial studies to assess patient course, response to therapy, and left ventricular remodeling. Furthermore, an analysis of images throughout the cardiac cycle may make additional information on the synchrony of left ventricular contraction available for patient care; such information has been shown to improve diagnostic accuracy compared to analysis of end systolic function alone.

Manual tracing of ventricular contours from the multiple images of a patient's heart is tedious and time consuming, requiring some 12–15 hours per patient study. Quantitative analysis of such three-dimensional studies is thus impractical for routine patient care or in situations when time is of the essence. Furthermore, such image interpretation requires specialized training and experience on the part of the technician doing the tracing and is subject to variability and human error. Even two-dimensional image analysis methods are infrequently utilized in clinical practice, because hospital personnel lack the time to manually trace the ventricular contours in even just one or two imaging planes. It is therefore evident that application of these techniques for the quantitative analysis of three-dimensional echocardiographic images to patient care is not feasible unless contour delineation can be automated, so that results can be rapidly obtained.

Much effort has been expended over the past 15 years to develop an automated contour delineation algorithm for echocardiograms. The task is difficult because ultrasound images are inherently subject to noise, and the endocardial and epicardial contours comprise multiple tissue elements. Most of the research has been devoted to detection of contours from two-dimensional echo images. At first, attempts were made to trace the ventricular contour from static images. The earliest algorithms were gradient based edge detectors that searched among the gray scale values of the image pixels for a transition from light to dark, which might correspond to the border between the myocardium and the blood in a ventricular chamber. It was then necessary to identify those edge segments that should be strung together to form the ventricular contour. This task was typically performed by looking for local shape consistency and avoiding abrupt changes in contour direction. The edge detectors were usually designed to search radially from the center of the ventricle to locate the endocardial and epicardial contours. These prior art techniques were most applicable to short axis views. The application of an elliptical model enabled contour detection in apical views in which the left ventricle appears roughly elliptical in shape; however, the irregular contour in the region of the two valves at the basal end could not be accurately delineated. Another problem with some of the early edge detectors was that they traced all contours of the ventricular endocardium indiscriminately around and between the trabeculae carneae and papillary muscles. Subsequent methods were able to ignore these details of the musculature and to trace the smoother contour of the underlying endocardium.

Contour delineation accuracy improved when algorithms began to incorporate information available from tracking the motion of the heart as it contracts and expands with each beat during the cardiac cycle, instead of operating on a single static image. Indeed, human observers almost always utilize this type of temporal information when they trace contours manually. Similarities between temporally adjacent image frames are used to help fill in discontinuities or areas of signal dropout in an image, and to smooth the rough contours obtained using a radial search algorithm. The problems with these prior art methods are that: (a) the user generally has to manually trace the ventricular contour or identify a region of interest in the first image of the time series, (b) the errors at any frame in the series may be propagated to subsequent frames, and (c) the cardiac parameters of greatest clinical interest are derived from analysis of only two time points in the cardiac cycle—end diastole and end systole—and do not require frame by frame analysis.

Another way to utilize timing information is to measure the velocity of regional ventricular wall motion using optical flow techniques. However, wall motion and wall thickening are the parameters used clinically to evaluate cardiac status, not velocity. Also, such velocity measurements are very much subject to noise in the image, because the change in gray level from one image to the next may be caused by signal dropout or noise, rather than by the motion of the heart walls. The effect of this noise cannot be reduced by data smoothing over time because of the low frame rate (30 frames per second) relative to the heart rate (60–100 beats per minute).

The algorithm developed by Geiser et al. in "A Second-Generation Computer-Based Edge Detection Algorithm for Short Axis, Two-Dimensional Echocardiographic Images: Accuracy and Improvement in Interobserver Variability," J. Am. Soc. Echo 3:79–90 (1990) is much more accurate in contour delineation than those previously reported. The Geiser et al. algorithm incorporates not only temporal information, but also knowledge about the expected homogeneity of regional wall thickness by considering both the endocardial and epicardial contours. In addition, knowledge concerning the expected shape of the ventricular contour is applied to assist in connecting edge segments together into a contour. However, this method cannot be applied to three-dimensional echocardiograms, because the assumptions concerning ventricular shape are specific for standard two-dimensional imaging planes, such as the parasternal short axis view at mid ventricle, or the apical four chamber view. In a three-dimensional scan, the imaging planes may have a variety of locations and orientations in space. Another problem is that one of the assumptions used to select and connect edge segments—that the contour is elliptical—may not be valid under certain disease conditions in which the curvature of the interventricular septum is reversed.

Another way to use heart shape information is as a post processing step. As reported in "Automatic Contour Definition on left Ventriculograms by Image Evidence and a Multiple Template-Based Model," IEEE Trans. Med. Imag. 8:173–185 (1989), Lilly et al. used templates based on manually traced contours to verify the anatomical feasibility of the contours detected by their algorithm, and to make corrections to the contours. This method has only been used for contrast ventriculograms, however, and is probably not applicable to echocardiographic images.

Automated contour delineation algorithms for three-dimensional image sets at first merely extended the one and two-dimensional gradient based edge detectors to the spatial dimension. Some authors found edges in the individual two-dimensional images and then connected them into a three-dimensional surface. Others found edges based on three-dimensional gradients. However, as was seen in dealing with two-dimensional images, the problem is not to find gray scale edges, but rather to identify which of the many edges found in each image should be retained and connected to reconstruct the ventricular surface. A number of investigators have moved from connecting contour segments using simple shape models based on local smoothness criteria in space and time, to starting with a closed contour and deforming it to fit the image. An advantage of this approach is that the fitting procedure itself produces a surface reconstruction of the ventricle.

In their paper entitled, "Recovery of the 3-D Shape of the Left Ventricle from Echocardiographic Images," IEEE Trans. Med. Imag. 14:301–317 (1995), Coppini et al. explain how they employed a plastic surface that deforms to fit the gray scale information, to develop a three-dimensional shape. However their surface is basically a sphere pulled by springs, and cannot capture the complex anatomic shape of the ventricle with its outflow tract and valves. Other models have been developed, which are based on parametric functions, superquadratics, or finite element models, but these models require many terms to accurately represent complexities in ventricular shape, such as the sharp edges at the junction of the mitral valve annulus and the left ventricle, and the left ventricular outflow tract. This limitation is important because, although the global parameters of volume and mass are relatively insensitive to small localized errors, analysis of ventricular shape and regional function require accurate contour detection and reconstruction of the ventricular surface.

Another prior art approach is the active contour model or "snake," which deforms a closed contour under the influence of external forces to fit the gray scale features in an image. Three-dimensional active contour models have been developed; however, active contour models have limited accuracy due to their basis in geometric rather than anatomical models. They may produce anatomically implausible contours, because it is difficult to incorporate anatomical knowledge into the search for an accurate contour. Herlin et al. had to track the contour frame by frame through a cardiac cycle to prevent their active contour model from crossing into the left atrium when the mitral valve was open during diastole ("Performing Segmentation of Ultrasound Images Using Temporal Information," Proceedings 1993 IEEE Computer Society Conference on Computer Vision and Pattern Recognition, New York City, pp. 373–378). Individual segments of the contour can be constrained to specified shapes, but the model does not provide for any description of the interaction of the segments with each other to form an anatomically possible contour. Another problem is that for identification of complex structures such as the heart, the user may need to interact with the algorithm, to guide it or to initialize the fitting procedure. Finally, these models are difficult to apply to imaging planes that are randomly oriented in space, being more appropriate for images in parallel planes or images derived from rotational scans at fixed angular intervals.

One of the newer contour detection methods utilizes a knowledge based model of the ventricular contour called an active shape model. (See T. F. Cootes, A. Hill, C. J. Taylor, and J. Haslam, "Use of Active Shape Models for Locating Structures in Medical Images," which is included in *Information Processing Medical Imaging*, edited by H. H. Barrett and A. F. Gmitro, Berlin, Springer-Verlag, pp. 33–47, 1993.) Like active contour models, active shape models use an iterative refinement algorithm to search the image. The principal difference is that the active shape model can only be deformed in ways that are consistent with the statistical model derived from training data. This model of the shape of the ventricle is generated by performing a principal components analysis of the manually traced contours from a set of training images derived from ultrasound studies. The contours include a number of landmarks, which are consistently located, represent the same point in each study, and have gray scale characteristics that are determined from the training data. Automated contour detection is performed by searching the image for contour segments that match the landmarks in the model. This approach was developed for two-dimensional images acquired in standard imaging planes, but can also be applied to images in a single plane frame by frame through time, and through contiguous parallel planes in three-dimensional space when the change in the shape of the target organ between planes is small. However, no evidence has been provided to show that a three-dimensional model can be developed by this technique, or that the three-dimensional surface generated by this modeling technique accurately reconstructs the three-dimensional shape of the ventricle. Indeed, because this approach estimates the gray scale appearance of the target organ empirically, it cannot be applied to randomly oriented imaging planes.

Accordingly, it will be evident that there is a need for a new approach to automated contour delineation for three-dimensional reconstruction of cardiac structures from ultrasound scans, an approach that correctly identifies and delineates segments of the ventricular contours in a plurality of imaging planes, enabling an anatomically accurate reconstruction of the ventricular surface to be produced. The method used in this novel approach should not assume any fixed relationship between imaging planes, but instead should be applicable to images from any combination of imaging plane locations and orientations in space. In addition, the method should be applicable to reconstructing both the endocardial and epicardial contours, and to images acquired at any time point in the cardiac cycle.

SUMMARY OF THE INVENTION

In accordance with the present invention, a method for delineating a three-dimensional surface of a patient's heart includes the step of imaging the patient's heart to produce imaging data that define a plurality of observed images along a corresponding plurality of image planes extending through the patient's heart. The method employs a three-dimensional mesh model derived from training data collected by imaging and tracing shapes of a plurality of other hearts. A plurality of predefined anatomical locations in the patient's heart are identified in the observed images, and the mesh model is then rigidly aligned with the images in the image planes, in respect to these predefined anatomical locations. Predicted images are produced from the mesh model as rigidly aligned in the image planes of the observed images. The predicted images are successively optimized by repetitively adjusting the mesh model to reduce differences between the predicted images and the observed images. The method produces a mesh model output of the patient's heart.

The step of imaging preferably comprises the step of producing ultrasonic images of the heart using an ultrasonic imaging device disposed at known positions and orientations relative to the patient's heart. In addition, the patient's heart is preferably imaged at a plurality of times during a cardiac cycle, including at an end diastole and at an end systole.

The mesh model is based upon an archetype shape derived from shapes of the plurality of the training data hearts and on a estimated covariance matrix that indicates the extent of variation in three dimensions for each of a plurality of control vertices. The step of rigidly aligning comprises the steps of rigidly rotating and translating, and scaling the mesh model as necessary to position and orient the mesh model so that anatomical locations in the predicted images are generally matched to the corresponding anatomical locations that were identified in the observed images of the patient's heart.

To optimize the fit of the predicted images to the images in the imaging data for the patient, the control vertices of the mesh model are reiteratively adjusted so that a set of predicted image features generated using the adjusted mesh model closely matches corresponding features of the observed images. Each iteration of the optimization preferably works on a subgroup of the control vertices. The subgroups are defined so that control vertices associated with adjusting a common portion of the mesh are not assigned to the same subgroup. Each step of optimization measures an area between anatomical features in the predicted images and anatomical features in the observed images. New predicted images are generated after each optimization adjustment. In addition, the method preferably includes the step of determining if the shape of the three-dimensional surface of the model following its adjustment is clinically probable, and if not, a user may elect to manually edit the mesh model. In a preferred application of the invention, the three-dimensional surface is of a left ventricle of the patient's heart. Preferably, the three-dimensional surface obtained in the disclosed application of the present invention is determined for different parts of a cardiac cycle.

A further aspect of the present invention is directed to a method for diagnostically evaluating and analyzing physiological functions of an in vivo organ using the image data, based upon a determination of the contour of the organ and its change between different time points in the cardiac cycle, for example, between end diastole and end systole. By observing the manner in which the contour changes during the cardiac cycle, the physiological function of the organ can be evaluated. Thus, by studying the contour changes, a medical practitioner might determine whether a muscle comprising a wall of the heart is weak. Evaluation of the contour of the ventricle at a single point in time generally cannot provide equivalent information to a medical practitioner.

Yet another aspect of the present invention is directed to a method for creating a three-dimensional reconstruction of at least a portion of a patient's heart. This method employs steps that are generally consistent with the steps noted above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

Figure 2:
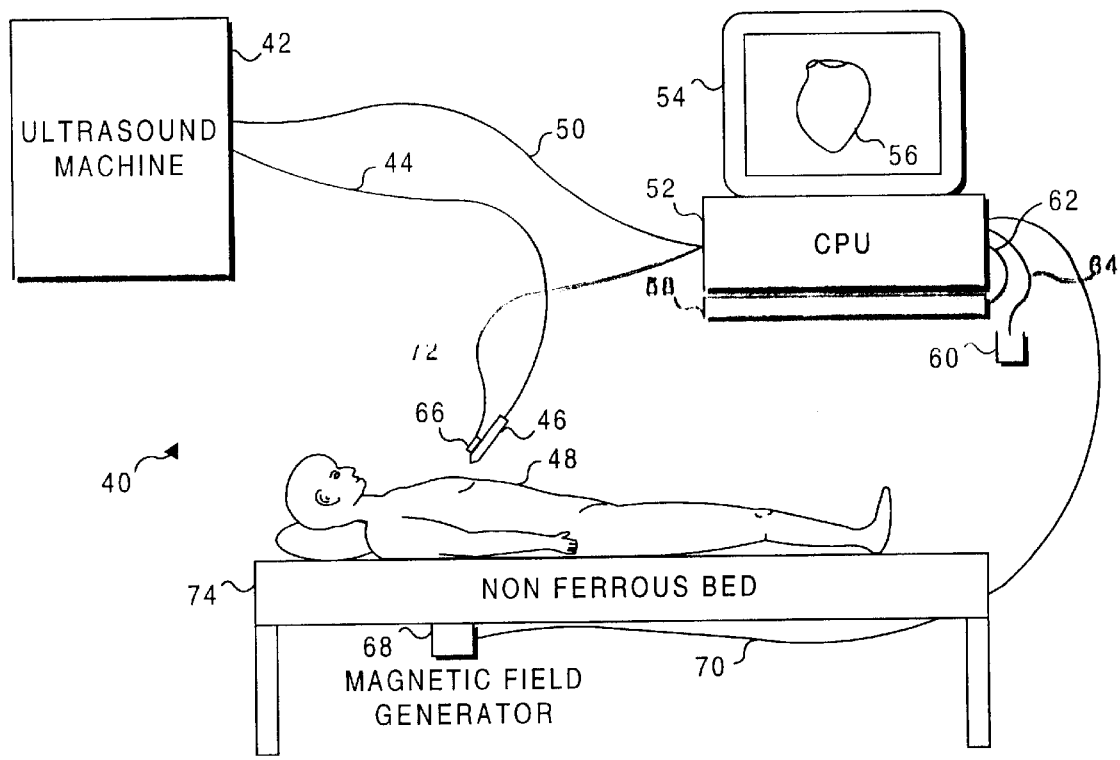
FIG. 2 illustrates a block diagram of a system in accordance with the present invention, for use in imaging the heart of a patient and to enable analysis of the images to determine cardiac parameters.

While the present invention is expected to be applicable to imaging data produced by other types of imaging modalities, in a preferred embodiment discussed below, ultrasound imaging is employed to provide the imaging data. With reference to FIG. 2, a system 40 is shown for producing ultrasonic images of a patient's heart that are usable for producing a three-dimensional representation of the surface of at least a portion of the heart. This system includes a central processing unit (CPU) 52 (i.e., a personal computer or graphic workstation terminal) that is coupled to a graphics display 54, and via a cable 62, to a keyboard 58 employed for input of data or instructions controlling the image processing and modeling procedures used to determine cardiac parameters in accordance with the present invention. In addition, a mouse 60 (or other cursor manipulation and pointing device) is coupled to CPU 52 via a cable 64, for use in graphically controlling the software running on CPU 52, for example, for selection of menu items, or for manually tracing images produced on graphics display 54, as explained below.

An ultrasound transducer 46 is driven to produce ultrasound waves in response to a signal conveyed from an ultrasound machine 42 over a cable 44. The ultrasound waves produced by ultrasound transducer 46 propagate into the chest of a patient 48 and are reflected back to the ultrasound transducer, conveying image data indicating the spatial disposition of organs, tissue, and bone within the patient's body that reflect the ultrasound signal differently. The reflected ultrasound waves are converted into a corresponding signal by ultrasound transducer 46, and this signal, which conveys the reflected image data, is conveyed to ultrasound machine 42 over cable 44 and converted to an analog image signal by an ultrasound imaging processor (not shown) disposed within the ultrasound machine.

Within CPU 52 (and thus also not shown) is an analog-to-digital converter (ADC). The ADC receives the analog image signal that is produced by the ultrasound imaging processor and conveyed to the ADC over a lead 50, and produces a corresponding digital signal that is used by CPU 52 to produce an ultrasound image 56 appearing on graphics display 54.

Of primary interest in regard to the present invention are the ultrasound reflections from the heart of patient 48. As shown in FIG. 2, the ultrasound transducer is generally positioned on the patient's chest so that the ultrasound waves emitted by the sensor propagate through the heart of the patient. However, there is no requirement to position the ultrasound transducer at any specific angle or to position it at any specific place, since its orientation and position are monitored and recorded, as explained below.

CPU 52 also receives a digital signal from a position and orientation sensor 66 over a lead 72, which is correlated with the image produced by ultrasound machine 42 that is received by the ADC. Position and orientation sensor 66 produces a signal responsive to a magnetic field produced by a magnetic field generator 68, which is mounted under a non-ferrous bed 74 on which the patient is reclining. Use of a non-ferrous bed avoids any magnetic shielding of position and orientation sensor 66 that might otherwise arise due to the ferrous bed components that are typically used in a conventional bed.

Since the position and orientation sensor is attached to ultrasound transducer 46, it provides a digital signal indicative of the position and orientation of the ultrasound transducer relative to the magnetic field generator. The time varying position and orientation of the ultrasound transducer relative to magnetic field generator 68 comprise data that are stored in a non-volatile memory (e.g., on a hard drive—not separately shown) by CPU 52, along with other data indicative of the pixels comprising the ultrasound images of the patient's heart (or other organ). Thus, the position and orientation data define the position and orientation of the ultrasound transducer at the time each image frame is recorded by the CPU and thereby enable the CPU to compute the three-dimensional coordinates of every pixel comprising each image frame relative to the coordinate system of magnetic field generator 68.

The patient's heart (or other organ) is preferably imaged with ultrasound transducer 46 disposed at two or more substantially different positions (e.g., from both the front and side of the patient's chest) and at multiple orientations at each position so that the resulting imaging data include images for a plurality of different imaging planes. The images are recorded at a plurality of time points in a cardiac cycle including, at a minimum, an end diastole, when the heart is maximally filled with blood, and an end systole, when the heart is maximally contracted. Each image comprises a plurality of pixels, each pixel having a gray scale value. The images preferably include a region of interest in which the left (or right) ventricle is disposed, since most information of interest relating to the condition of the patient's heart is obtained by analyzing the three-dimensional contours of this portion of the heart. However, it should be emphasized that although the preferred embodiment of the present invention is disclosed, by way of example, in connection with automatically determining the endocardial and epicardial contours of the left ventricle as three-dimensional surfaces, the invention is equally applicable and useful in automatically determining the contours of other chambers of the heart, so that other parameters generally indicative of the condition of the patient's heart can be evaluated, as discussed hereinbelow, or the contours of other organs in the patient's body.

It may be helpful to briefly discuss the mathematical theory that defines the process for producing the image data used in this invention. The equation governing the reflection of sound at a specular boundary is given by:

$$I_r = I_i \left( \frac{Z_2 \cos\theta_i - Z_1 \cos\theta_t}{Z_2 \cos\theta_i + Z_1 \cos\theta_t} \right)^2 \tag{1}$$

where: $I_r$ is the reflected intensity, $I_i$ is the incident intensity, $Z_1$ is the characteristic impedance in medium 1, $Z_2$ is the characteristic impedance in medium 2, $\theta_i$ is the angle of incidence, which is the angle between a surface normal at the interface between the two media and the direction of an incident sound beam, $\theta_r$ is the angle of reflection, which is the angle between a surface normal at the interface between the two media and the direction of a reflected sound beam, and $\theta_t$ is the angle of transmission, which is the angle between a surface normal at the interface between the two media and the direction of a transmitted sound beam (all angles being between 0° and 90°). The transmitted sound intensity through a boundary between two media is given by:

$$I_t = I_i - I_r = I_i 4 Z_2 Z_1 \cos^2 \frac{\theta_i}{(Z_2 \cos\theta_i + Z_1 \cos\theta_t)^2} \tag{2}$$

Accordingly, an intensity reflection coefficient $\alpha_r$ and an intensity transmission coefficient $\alpha_t$ of the interface between medium 1 and medium 2 are defined as:

$$\alpha_r(\theta_i, \theta_t) = \left( \frac{Z_2 \cos\theta_i - Z_1 \cos\theta_t}{Z_2 \cos\theta_i + Z_1 \cos\theta_t} \right)^2, \tag{3}$$

$$\alpha_t(\theta_i, \theta_t) = \frac{4 Z_2 Z_1 \cos^2 \theta_i}{(Z_2 \cos\theta_i + Z_1 \cos\theta_t)^2} \tag{4}$$

To determine the reflected intensity of a sound wave from a surface such as the epicardial surface of the heart, the specular reflection and diffuse reflection are incorporated into a single equation, as follows:

$$I_r = I_i \left( \frac{Z_2 - Z_1}{Z_2 + Z_1} \right)^2 \cos^n \theta_i, \tag{5}$$

The intensity received by the ultrasound transducer from a specific point being observed in the imaging plane is either:

$$I_{received}(l, \theta) = I_{sent} \left[ \exp\left(-4 \sum_{i=1}^{N} \alpha_i l_i \right) \right] \left[ \prod_{i=1}^{N-1} \alpha_t^2(\theta_i) \right] \left( \frac{\eta_b}{l^2} \right), \tag{6}$$

when the point to be observed is not on the structure boundary, or:

$$I_{received}(l, \theta) = I_{sent} \left[ \exp\left(-4 \sum_{i=1}^{N} \alpha_i l_i \right) \right] \left[ \prod_{i=1}^{N-1} \alpha_t^2(\theta_i) \right] \alpha_r(\theta_N) \cos^n \theta_N, \tag{7}$$

when the point to be observed is on the structure boundary, where $I_{received}$ (l, θ) is the ultrasound intensity received by the ultrasound transducer for the point being observed at (l, θ) along the ultrasound beam, l is the distance from the ultrasound image sensor to the point, in the direction of the ultrasound beam, $I_{sent}$ is the intensity of the ultrasound beam transmitted by the ultrasound transducer, N is the total number of tissues the beam has passed through until it arrives at the point being observed, $\alpha_i$ is the attenuation coefficient in the $i_{th}$ tissue, $l_i$ is the length of the $i_{th}$ tissue along the direction of the ultrasound beam, $\alpha_t(\theta_i)$ is the intensity transmission coefficient at the interface between the $(i-1)_{th}$ tissue and $i_{th}$ tissue with an incident angle $\theta_i$, $\theta_i$ is the angle between the $i_{th}$ surface normal of the interface and the direction of incident ultrasound beam, and $\eta_b$ is the intensity backscattering coefficient of the tissue associated with the point being observed. It will be apparent that the relative intensities of each point or pixel in an ultrasound image are determined as noted above, so that the image displayed by the CPU on the display comprises a collection of pixels having differing gray scale values based on such intensities. These images are not clean lines, but instead, are somewhat indefinite areas with differing gray scale values. Thus, it is difficult to manually determine the contours of the epicardial and endocardial surface in such images.

Figure 3:
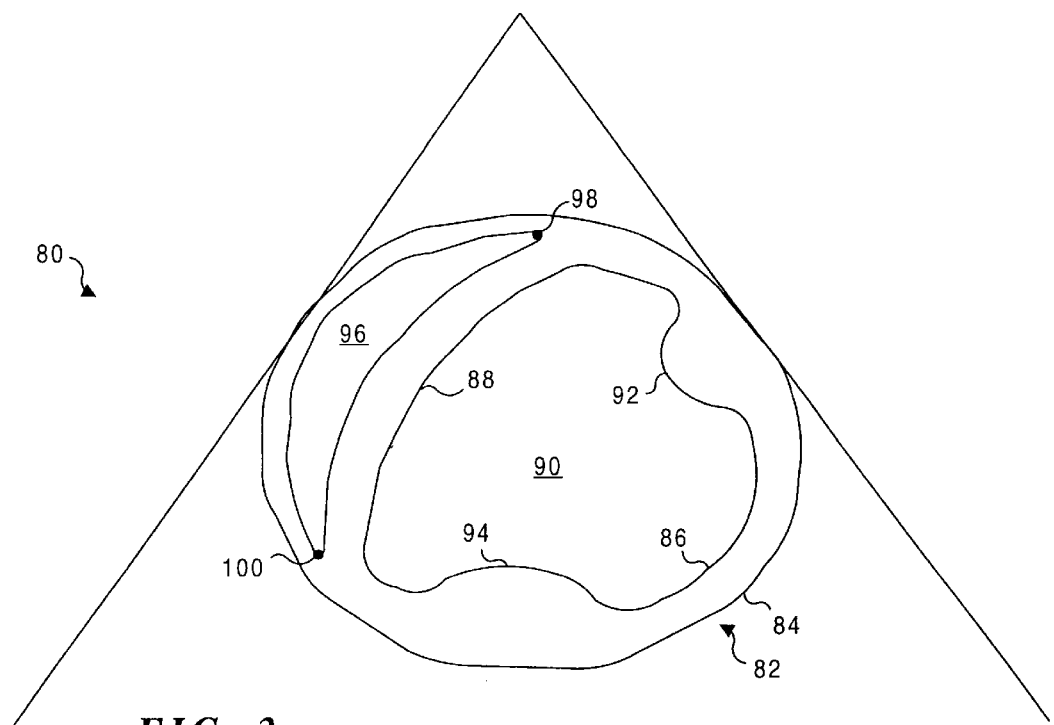
FIG. 3 is a schematic cross-sectional view of a left ventricle, as ultrasonically imaged along a transverse axis, indicating anatomic landmarks associated with the left ventricle.

A transverse or short axis view forming an image 80 of a left ventricle 82 in a patient's heart is shown in FIG. 3. An outer surface 84 (the epicardium) is clearly visible, as is an inner surface 86 (the endocardium). It must be stressed that this Figure and the other Figures discussed below schematically depict images in different ultrasound image planes, but do not show the gray scale data that would actually be seen in an ultrasound image. Thus, these Figures simply show the contours and the structure ol the heart included in their respective image planes. Also evident in FIG. 3 are anterior and posterior papillary muscles 92 and 94, a chamber 90 enclosed by the left ventricle, a right ventricle 96, and anterior and posterior septal points 98 and 100, respectively, which are used to identify the lateral bounds of a septum 88.

Figure 4:
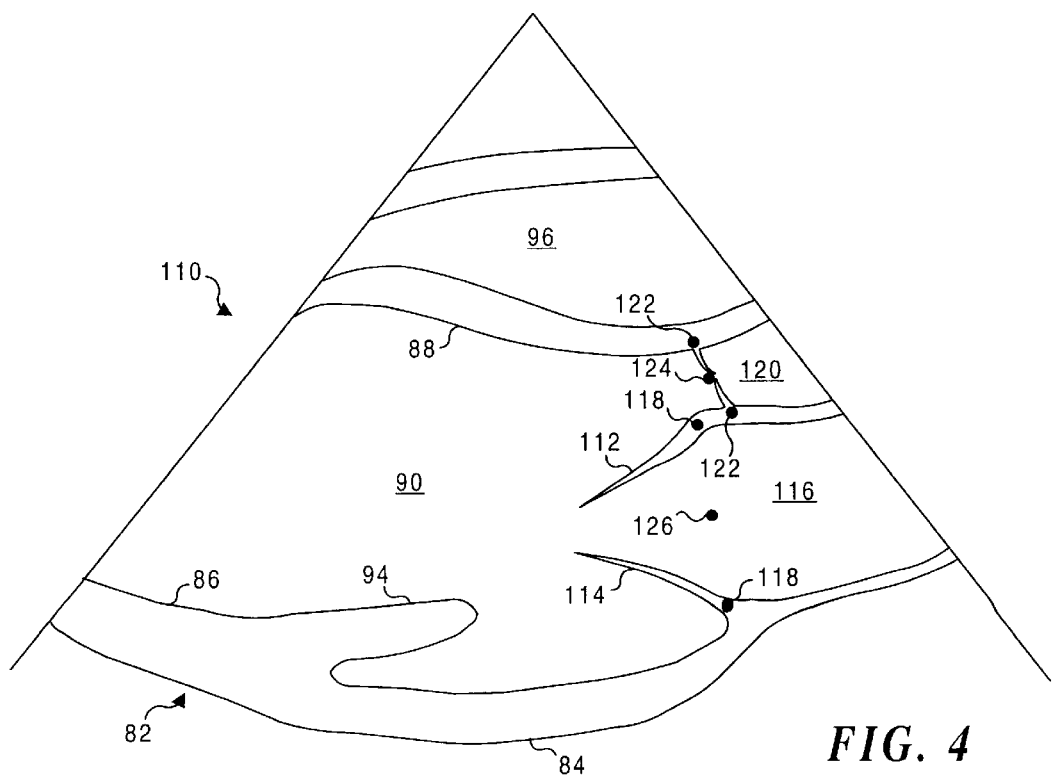
FIG. 4 is a schematic cross-sectional view of the left ventricle, as ultrasonically imaged along a longitudinal axis, indicating the anatomic landmarks associated with the left ventricle.

FIG. 4 shows a schematic representation 110 of an ultrasonic imaging system scan made in the parasternal long axis view of the patient's heart, principally focusing on a left ventricle 82, with its enclosed chamber 90. The left ventricle is defined by endocardium 86 and epicardium 84. Also indicated in the longitudinal axis view of FIG. 4 is an aortic valve 124 at the mouth of an aorta 120, whose junction with the left ventricle is marked by points 122. A portion of a left atrium 116 is visible at the right side of the ultrasonic scan image. Additional anatomic landmarks are mitral valve annulus points 118, anterior and posterior mitral valve leaflets 112 and 114, respectively, right ventricle 96, posterior papillary muscle 94, and interventricular septum 88.

Figure 5:
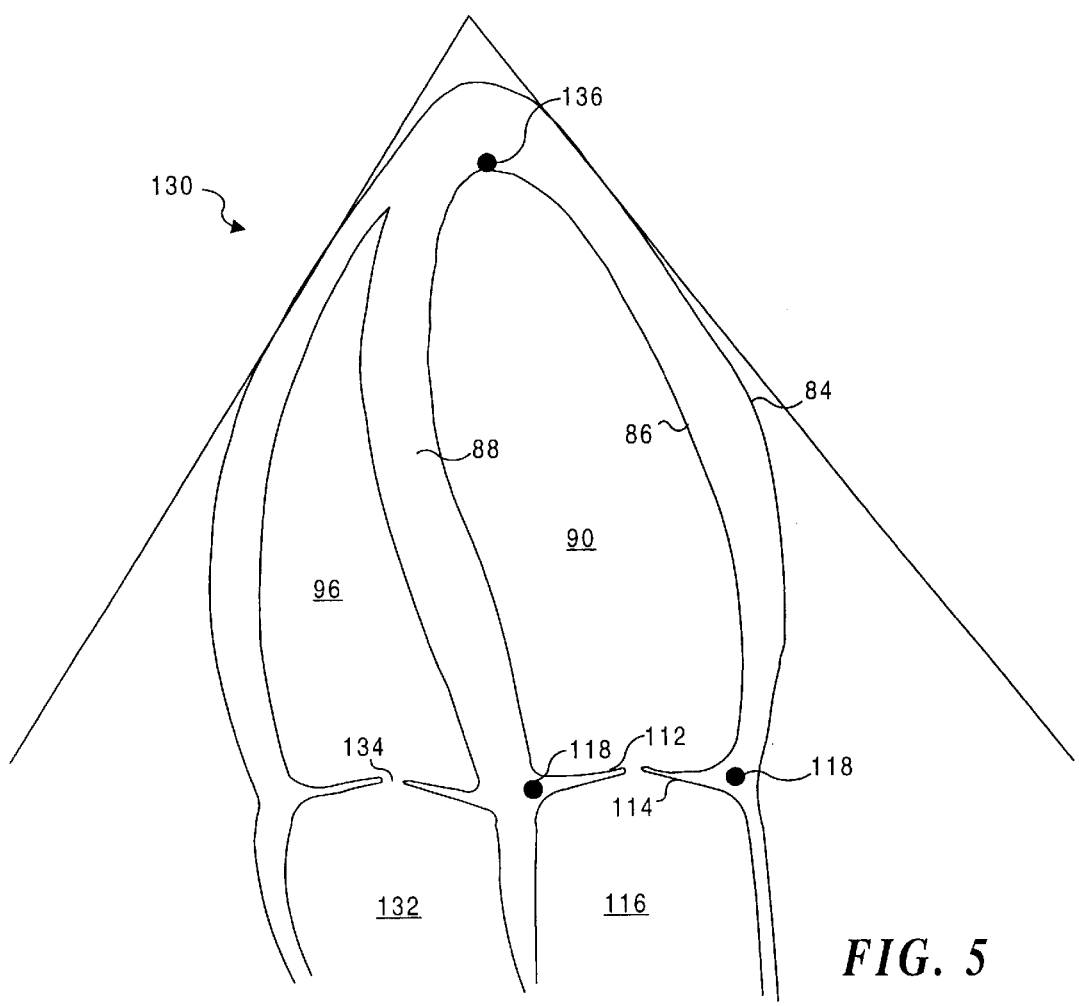
FIG. 5 is a schematic cross-sectional view of the left ventricle, ultrasonically imaged along a longitudinal axis, in a different plane from FIG. 4, indicating additional anatomic landmarks.

FIG. 5 shows a schematic representation 130 of an apical four chamber view of the patient's heart. In addition to the anatomic structures visible in the parasternal long axis view of FIG. 4, this apical view also shows a right atrium 132, a tricuspid valve 134, and an apex of the left ventricle 136.

Figure 6:
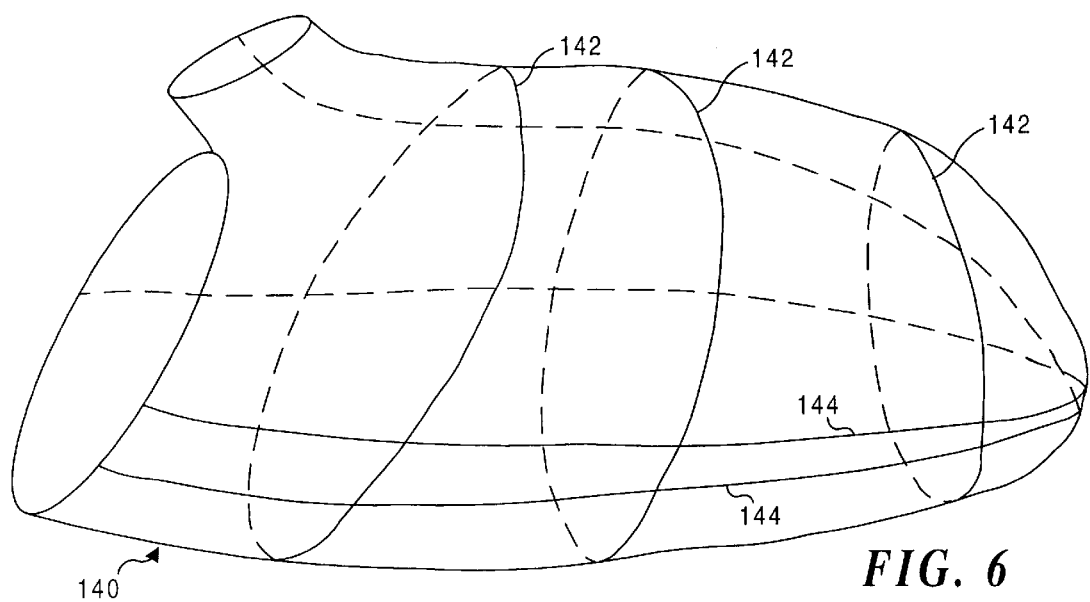
FIG. 6 illustrates the angled and rotational cross-sectional image planes obtained with a transcutaneous ultrasonic probe positioned in the parasternal and apical acoustic windows.

FIG. 6 illustrates some of the planes through a heart that may be imaged using the ultrasonic imaging sensor. These imaging planes may include a plurality of angulated planes 142 obtained from one or more ultrasonic imaging sensor positions and/or orientations, as well as rotated planes 144 that are obtained from a substantially different position and at different orientations of the ultrasonic imaging sensor.

Figure 1:
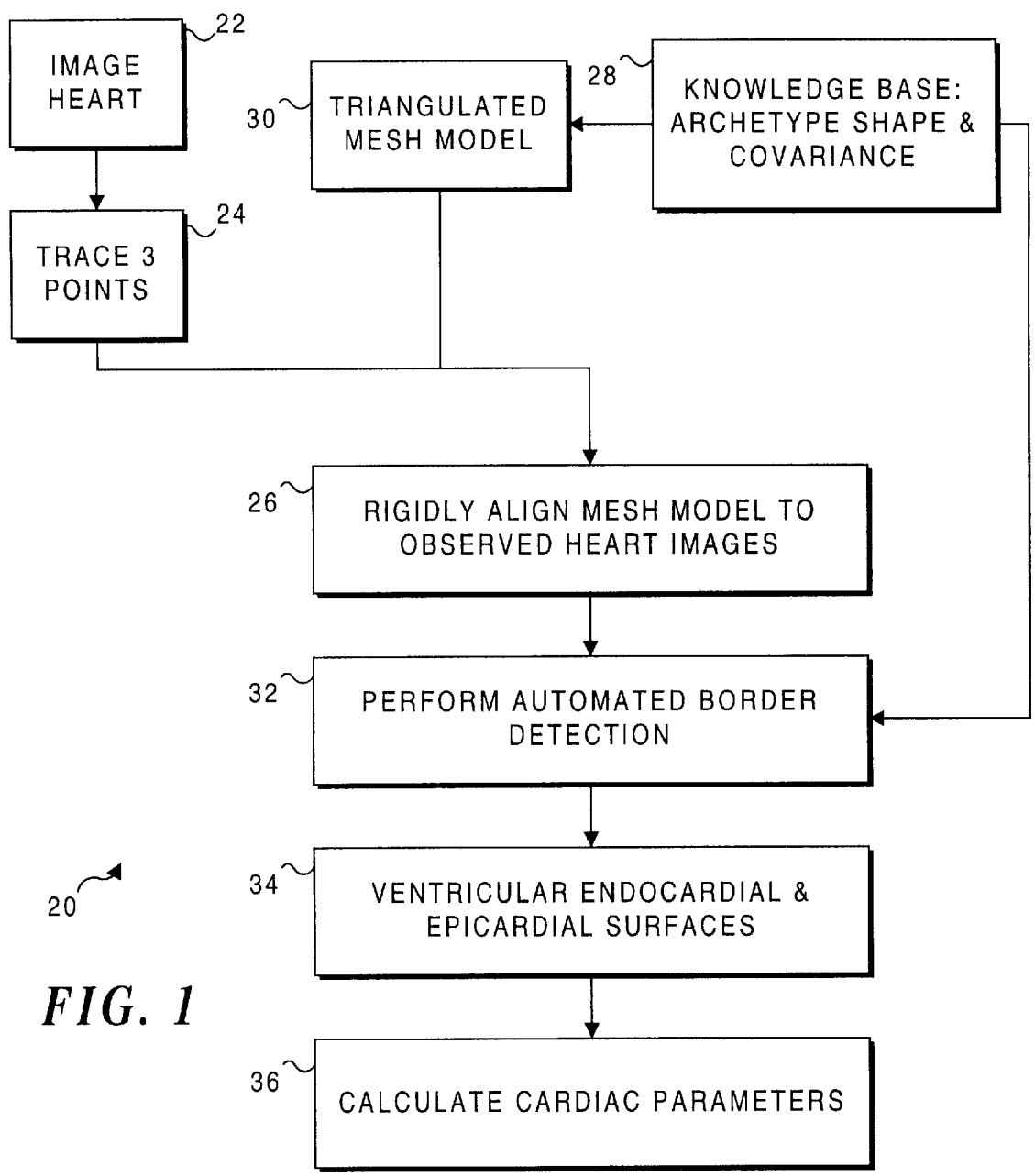
FIG. 1 is a top level or overview flow chart that generally defines the steps of Variation 1 of the method for automatically delineating the borders of the left ventricle from images.

FIG. 1 includes a top level or overview flow chart 20 that broadly defines the steps of a preferred method used in the present invention for automatically detecting the borders of the left ventricle of the heart and for producing a three-dimensional shape contour of that (or another portion of the heart) based upon the ultrasound scan of the heart of patient 48. In general, in a block 22 of FIG. 1, the image data for the heart are acquired by imaging the heart in multiple planes whose location and orientation in three-dimensional space are determined and recorded, as described above. In a block 24, three points representing specific anatomic landmark structures are manually traced in the images that were created in block 22, producing a set of three x,y,z coordinates. For the left ventricle, the specific anatomical landmarks are preferably a center of the aortic valve, a center of the mitral valve, and the ventricular apex.

Figure 7:
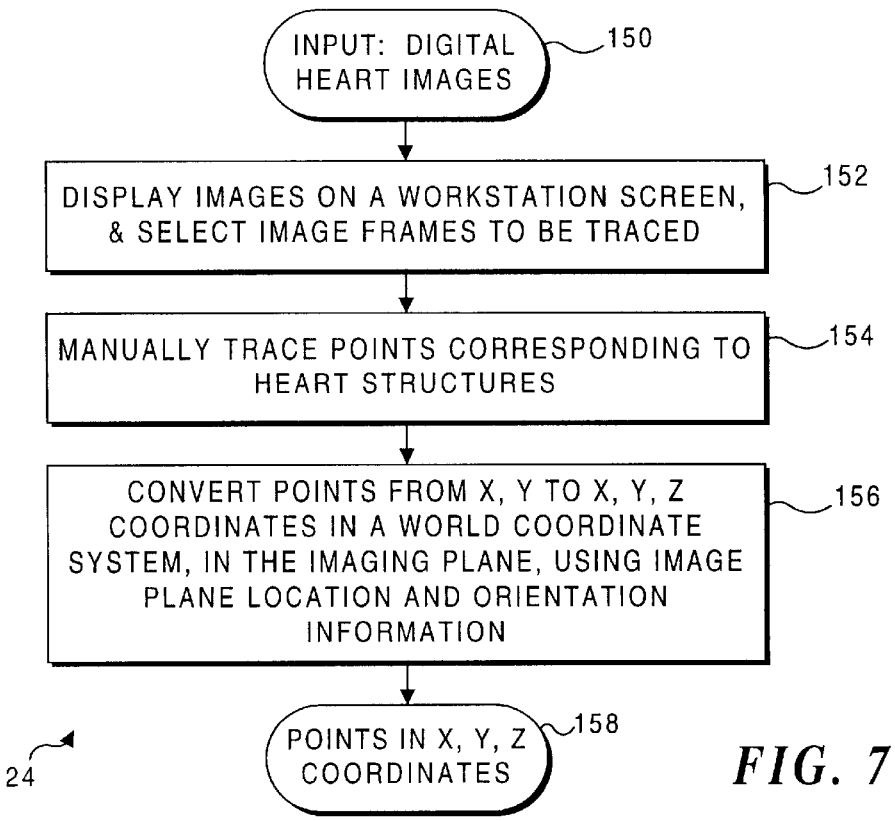
FIG. 7 is a flow chart illustrating the steps followed to manually trace anatomic landmarks from a heart image data set.

FIG. 7 illustrates details of block 24, for manually tracing anatomic structures or landmarks of the heart from ultrasound images (or from images produced by other imaging modalities). These images are reviewed on graphics display 54, and frames are selected for tracing the specific anatomic landmarks, at certain time points in the cardiac cycle, usually the time of end diastole, when the heart is maximally filled with blood, and the time of end systole, when the heart has reached maximum contraction, as noted in a block 152 in this Figure. To determine which images were scanned at a particular time during the cardiac cycle, an ECG can be recorded during the imaging process. The ECG will provide cardiac cycle data for each of the image planes scanned that is usable to identify the particular time in the cardiac cycle at which that image was produced. The identification of the time points is assisted also by review of the images themselves, to detect those image frames in which the cross-sectional contour of the heart appears to be maximal or minimal, respectively. The structures of interest are then located in the image and traced manually using mouse 60 or other pointing device, as indicated in a block 154. The x,y coordinates of the points demarcating the anatomic structures or landmarks of interest are converted into x,y,z coordinates in a block 158, using the position and orientation data recorded by magnetic field sensor 66, as noted in a block 156. Preferably, these anatomical landmarks include the apex of the left ventricle, the center of the aortic valve and the center of the mitral valve; other anatomical landmark structures that may be used include the papillary muscles and interventricular septum.

The present invention uses a set of training data to derive a mesh model of an archetype heart that is subsequently adjusted so that its shape "explains" the shape of the patient's heart in the observed images. A plurality of three-dimensional reconstructions of the left ventricles in a population of hearts exhibiting a wide variety of types and severity of heart disease is used to define a three-dimensional archetype shape of the left ventricle, and its range of shape variation (i.e., its covariance). Specifically, based on an analysis of this population of hearts, a knowledge base is developed in a block 28 and used to define the archetype shape of the left ventricle (or other portion of heart) and a covariance matrix defining the variability in the shape of this part of the heart, as observed in the population comprising the set of training data. Details of this procedure are illustrated in FIG. 10.

Figure 10:
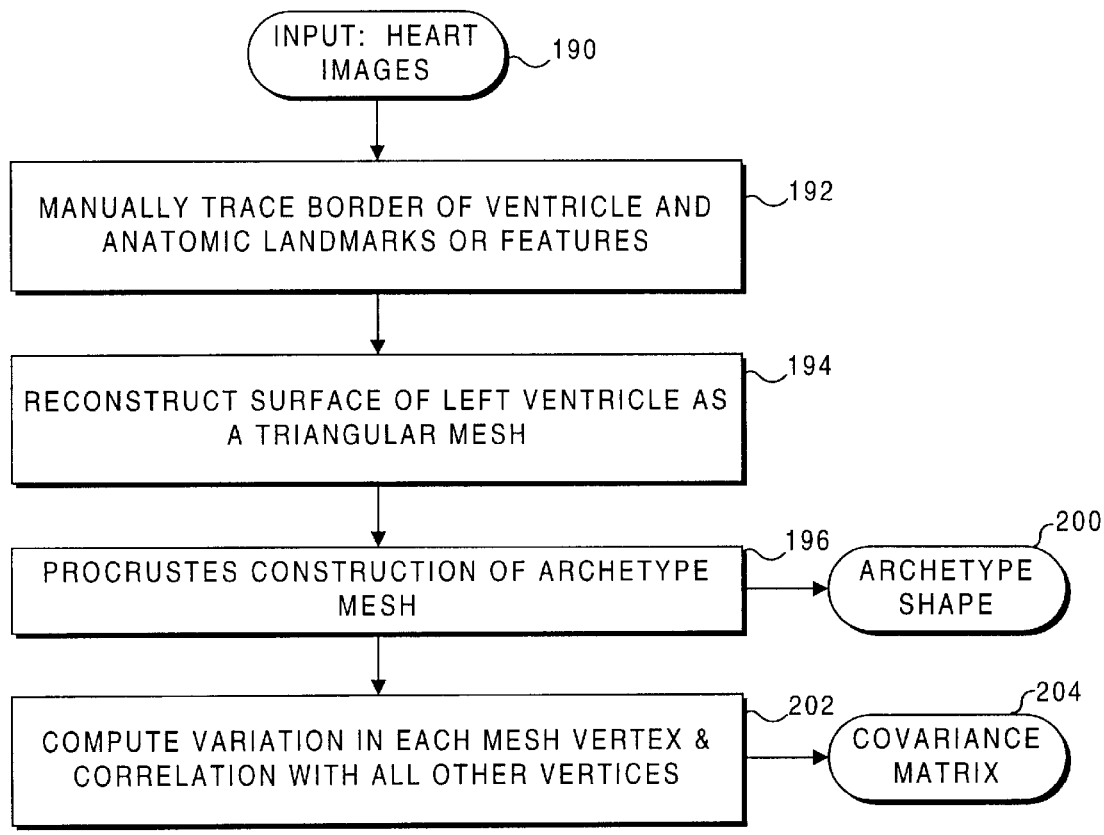
FIG. 10 is a flow chart illustrating the steps followed to generate the three-dimensional archetype shape and covariance matrix.

As shown in a block 192 of FIG. 10, the knowledge base is created by manually tracing ultrasound images 190 of the hearts (e.g., the left ventricle) for this group of other individuals, producing the set of training data. This manual tracing step employs much the same process as that shown in FIG. 7, for tracing the three anatomical landmarks in the patient's image data, but in addition to these three landmarks, the endocardium and/or epicardium surfaces, and additional landmarks are traced in the images of the hearts of the individuals to develop the set of training data. Preferably, the training data are developed by producing imaging data from at least three imaging planes for each of the hearts contributing to the training data set. The imaging data for each of these hearts comprise sequential image frames—sequential through time as well as through space. Each image in the training data comprises a plurality of pixels, and each pixel is disposed at a row and a column in the image associated with x,y,z coordinates relative to a coordinate system common to all images in the set.

Figure 8:
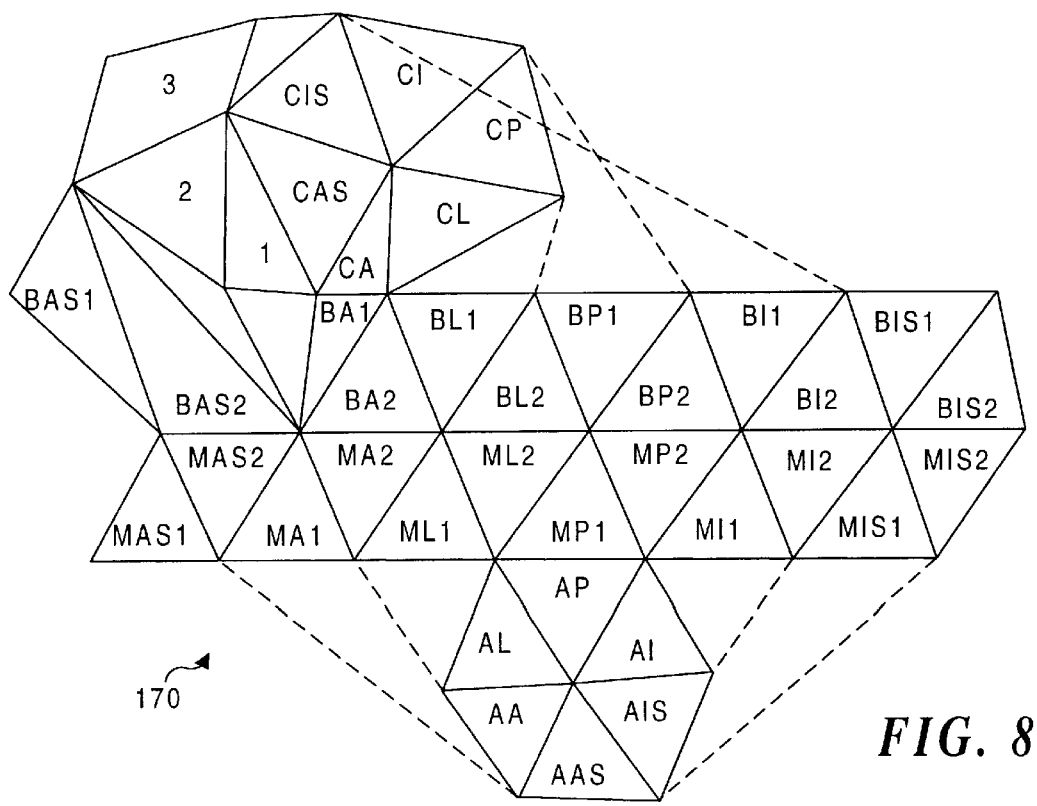
FIG. 8 illustrates an abstract control mesh for the left ventricle with faces labeled to indicate their association with anatomic landmarks.
Figure 9:
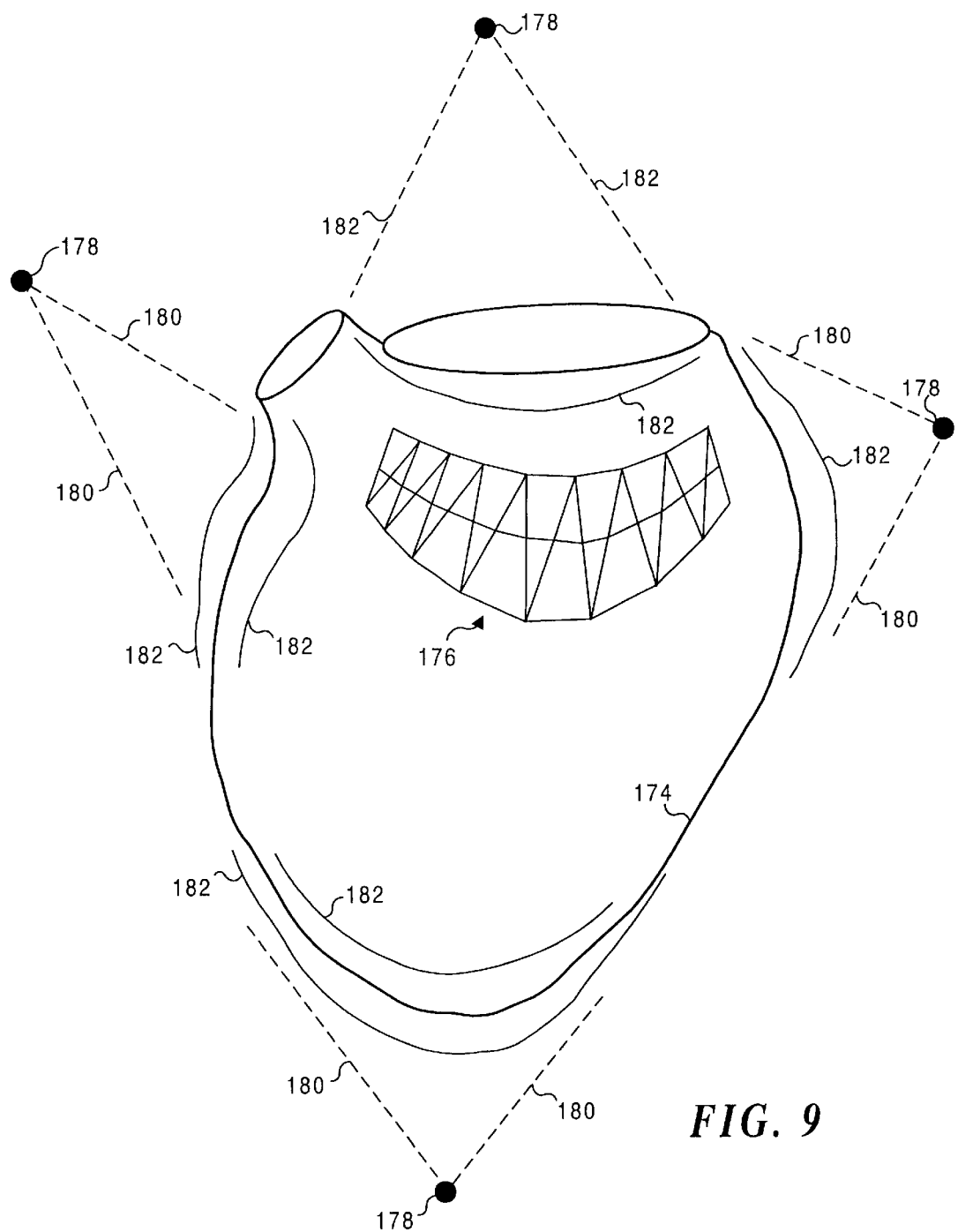
FIG. 9 is a schematic view showing a portion of a three-dimensional triangular mesh representing a left ventricular endocardial surface, and illustrating examples of control vertices used to control local variations in ventricular shape.

Each ventricular surface for the images comprising the training data is represented by an abstract three-dimensional triangular mesh, somewhat like mesh 170 shown in FIG. 8. The triangular faces of the abstract mesh in this Figure are labeled to indicate their association with anatomic landmarks. Thus, the triangular face labels AL, AP, AI, AIS, AAS, and AA all start with the letter "A" to indicate that they are associated with the apex region of the left ventricle. The shape of each ventricular surface is specified by a plurality of three-dimensional control vertices (not shown in FIG. 8). Triangles (initially about 37) comprising the abstract mesh are subdivided recursively to produce a smoother final surface having approximately 576 triangular faces in the preferred embodiment. However the shape of the subdivided surface is determined by the positions of the plurality of control vertices. In fitting the subdivided surface to the traced borders, the control vertices are repositioned as necessary. Currently, the preferred embodiment employs 27 control vertices or points.

This abstract mesh is developed by manually tracing the surfaces of the heart represented by the image planes and assembling the resulting data for use in preparing a three-dimensional reconstruction of the left ventricular endocardium and epicardium, as indicated in a block 194. Preferably, the three-dimensional triangular mesh used to represent the shape of the left ventricle is derived using a piecewise smooth subdivision method of surface reconstruction. As noted above, the mesh model that is thus generated is the abstract mesh, which is manually designed to fit the ventricles of a variety of normal and diseased hearts in the population on which the set of training data are based. When the abstract mesh is fit to the x,y,z coordinates of the ventricular contours and to the x,y,z coordinates of anatomic landmarks, every abstract vertex becomes associated with a three-dimensional point on the resulting embedded mesh. Through an iterative process, the fit of the embedded mesh to the input coordinates is improved. The abstract mesh used for the mesh model of the ventricular shape thus makes no assumptions concerning the geometry of the ventricle, but instead serves to define the relationships among the various anatomic landmarks. By adjusting the weights of energy terms related to the fitting function, local shape constraints can be applied during reconstruction to specific landmarks or regions on the ventricular surface. The anatomic landmarks may also be used to reference specific anatomic features that have singular gray scale attributes, or which represent the interface between different tissues, and are therefore particularly useful for automated contour delineation.

The manual tracing of heart borders from images in the set of training data can be assisted by utilizing a surface reconstruction algorithm in accord with block 194 in FIG. 10. In this algorithm, the user manually selects a representative subset of the imaging planes for tracing. The resulting borders are input into the reconstruction algorithm to produce a three-dimensional surface, which estimates the surface that would be obtained using borders traced from all imaging planes in the data set. The intersection of the estimated surface with the remaining imaging planes from which borders have not yet been traced is then calculated to produce a candidate border in each plane. The user can then inspect each candidate border and accept, edit, or retrace the border as necessary. It should be noted that this method for facilitating the manual analysis of a three-dimensional image set can be performed with any of a number of different algorithms for surface reconstruction, including an artificial neural network, although as noted above, the preferred approach employs a piecewise smooth subdivision method. It should be understood that this method for facilitating manual analysis can be applied for automated border detection to image data sets other than those selected for use as training data and may therefore be useful in other applications.

Using a "Procrustes-like" averaging algorithm, as indicated in a block 196, an archetype mesh is created so that the integral of the squared distances between the surface that the archetype mesh defines and the surfaces of rotated, transformed, and scaled training data meshes is minimized. Archetype shape 200 (i.e., the shape of the archetype mesh) is thus defined as a result of the Procrustes-like averaging algorithm. In a preferred embodiment of the present invention, as noted in a block 202, the anatomically allowable variations in ventricular shape are specified by an 81×81 covariance matrix 204 of a set of three-dimensional vertices for either the endocardial surface or the epicardial surface. The size of the covariance matrix is three times the number of control vertices, since each vertex has three spatial coordinates (x,y,z). This covariance matrix accounts for the degrees of variation in each matrix and its correlation with all other vertices as well.

To calculate the covariance matrix associated with the archetype shape, N given triangulated meshes having a fixed number K of vertices are referenced by $M_1, \ldots, M_N$, and ρ is a metric that measures an average distance between the surfaces defined by any two meshes. Further, for rotation matrices $R_n$, translation vectors $t_n$, and scale factors $s_n$, (for n=1, ..., N), a triangulated mesh M of K vertices and volume V is determined by an optimization procedure that minimizes:

$$\sum_{n=1}^{N} \rho^2(s_n(R_n M_n + t_n), M) \qquad (8)$$

If $v_{nk}$ is the vector from the $k_{th}$ vertex of M to the closest point on the surface of mesh $M_n$, the 81×81 covariance matrix is estimated by:

$$\text{covariance matrix} = \frac{1}{N} \sum_{n=1}^{N} \begin{pmatrix} v_{n1} \\ \vdots \\ v_{nk} \end{pmatrix} \begin{pmatrix} v_{n1} \\ \vdots \\ v_{nk} \end{pmatrix}' \qquad (9)$$

The knowledge base of three-dimensional ventricular shapes is thus defined to be the rotations, translations, and scaling of the set of training data, centered around the archetype shape, with the estimated covariance matrix for each of the vertices of the archetype shape.

Figure 11:
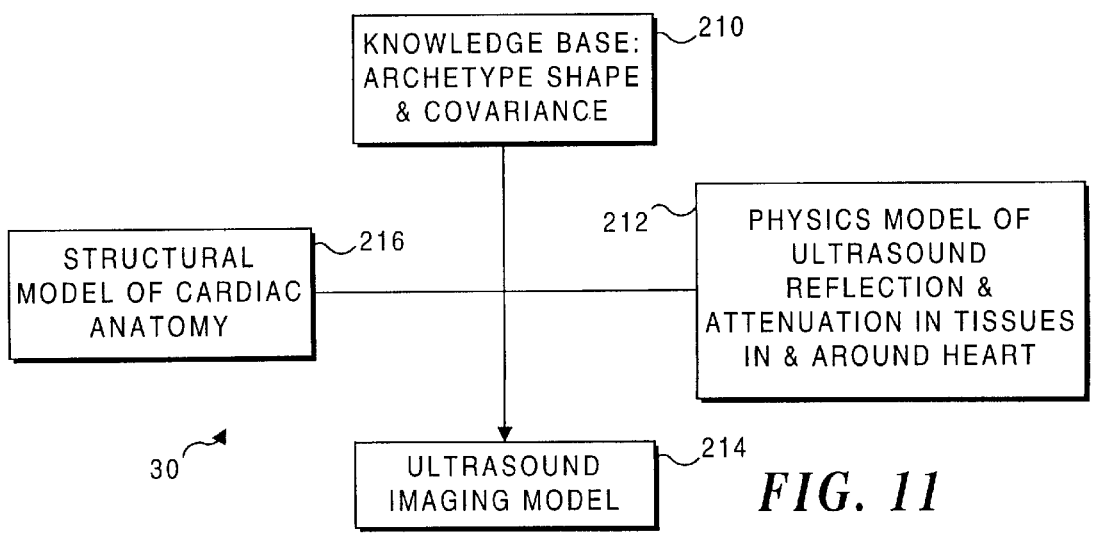
FIG. 11 is a chart that identifies the components of an ultrasound mesh model.

Referring back to FIG. 1, in a block 30, the ultrasound mesh model is developed from the knowledge base data, based upon knowledge concerning the process of ultrasound image formation. FIG. 11 provides further details. In this Figure, it will be apparent that an ultrasound mesh model 214 is determined based upon the archetype shape and covariance data (block 210), a physics model of ultrasound reflection and attenuation (block 212), generally as noted in Equations 1–6 above, and a structural model of cardiac anatomy 216. The ultrasound mesh model uses a physics model of ultrasound reflection in different tissues in and around the heart. The geometry of this model is based on the archetype shape and covariance matrix, which are embedded in the ultrasound mesh model in the form of a triangular mesh. The model takes into consideration parameters such as thickness of tissues, e.g., thickness of the myocardium and pericardium, a velocity with which ultrasound propagates in those tissues, their attenuation coefficients, a reflectivity of the tissues, and a smoothness of their surfaces, as well as parameters related to the imaging, such as a depth of the image, an angle of the scan sector, a frequency of the ultrasound, a lateral beam width, and a position of the beam relative to the heart. Clinical data are used to estimate parameters whose values are not available in the literature or obtainable from the imaging sensor, e.g., tissue attenuation and reflection.

Figure 12:
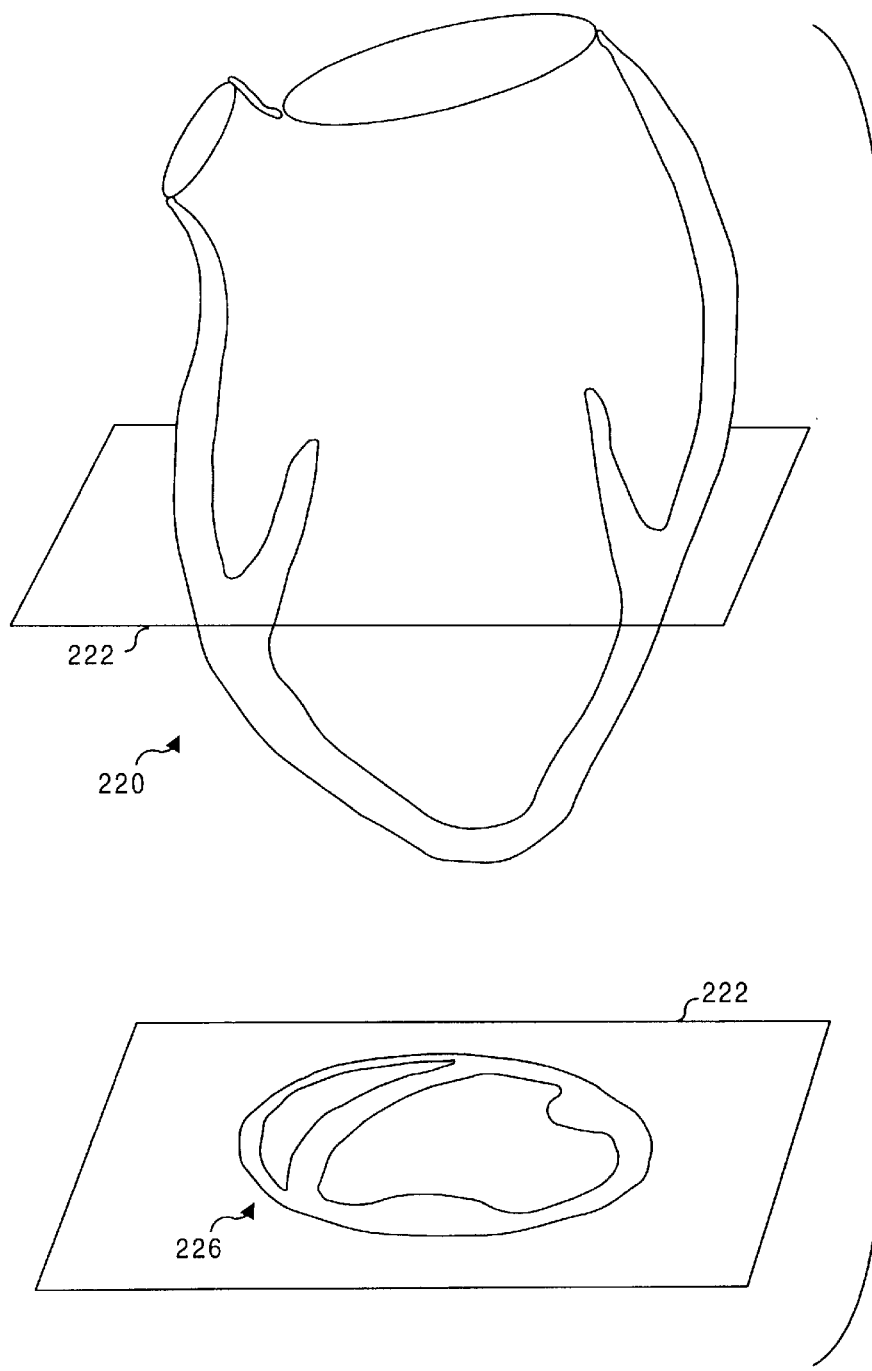
FIG. 12 is a schematic diagram of an ultrasound mesh model, which has been intersected by an imaging plane, illustrating how the model predicts the image for that plane.

In a block 26 in FIG. 1, the mesh representing the archetype shape is rigidly aligned to each of the images produced by imaging the heart of patient 48 using the three traced points or anatomical landmarks in each image. The ultrasound mesh model estimates an ideal gray scale appearance (i.e., a mean image) and an expected deviation (i.e., the covariance) from the ideal of any image in the patient's imaging data, given the location and orientation of the imaging plane at which the patient's heart was imaged, relative to the three-dimensional archetype shape. An example 220 of the ultrasound mesh model is shown in FIG. 12. When intersected by an imaging plane 222, the mesh model produces a gray scale image 226 that predicts the appearance of the ultrasound image in plane 222. In this manner, the mesh model is used to produce predicted images corresponding to the images of the patient's heart made in specific imaging planes. In a manner analogous to the rigid alignment step carried out in block 196 (FIG. 10) in regard to the meshes of the set of training data images, the mesh comprising the ultrasound image model is rigidly rotated and translated, and scaled as necessary to more closely align the anatomical landmarks in the predicted images derived from the mesh model with the corresponding anatomical landmarks in the corresponding images of the patient's heart.

Figure 13:
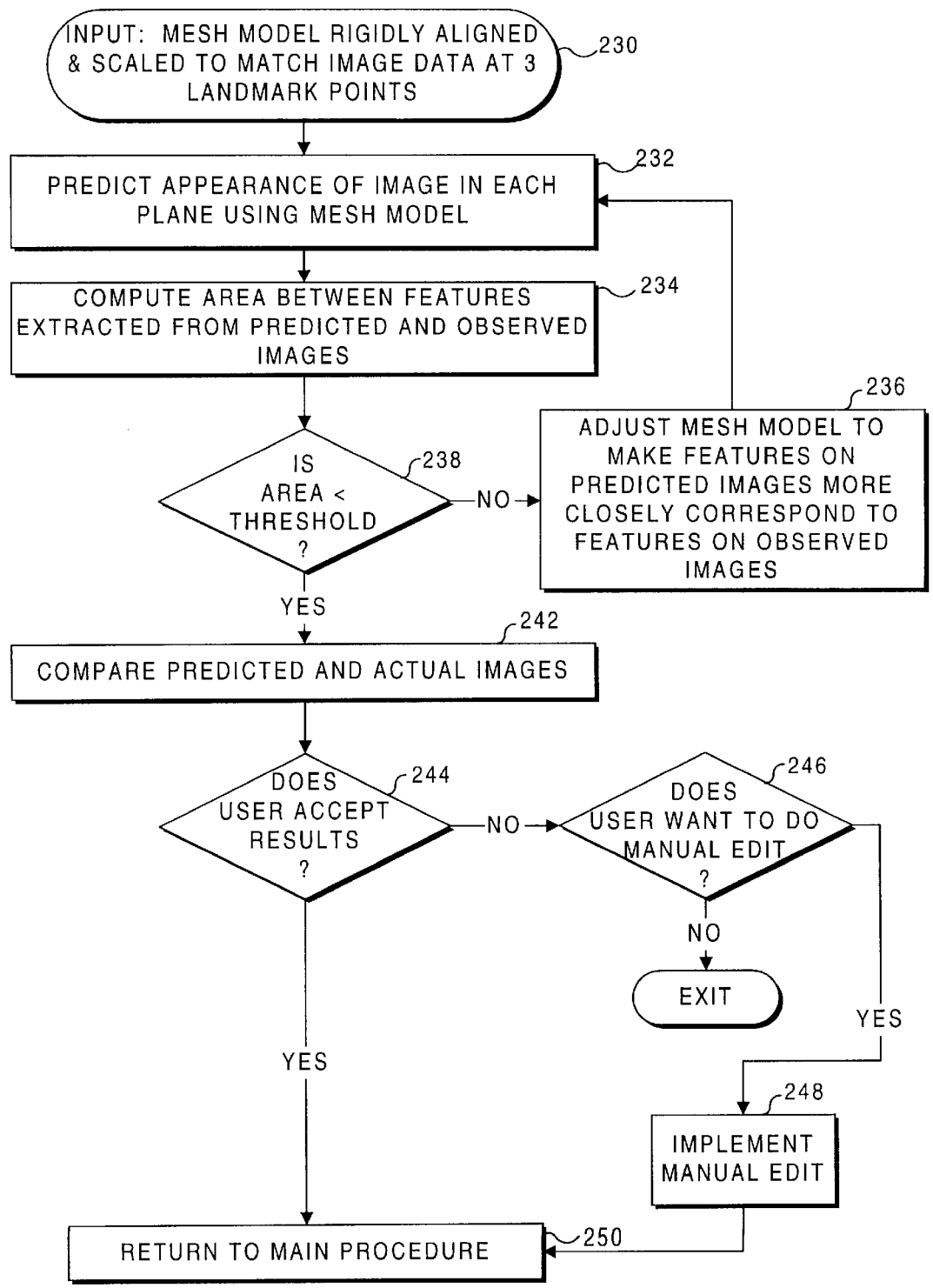
FIG. 13 is a flow chart illustrating the steps followed to optimize a fit of the images predicted by the ultrasound mesh model to the actual heart images, and to generate a three-dimensional mesh representing the automatically delineated ventricular surface.

In a block 32 of FIG. 1, automatic border detection is performed to enable further refinement of the match between the mesh model and the image data for patient 48. Automated border detection is performed by optimizing a fit of images predicted from the mesh model, to the patient's images. Details of this process are shown in FIG. 13, starting with a block 230 in which the mesh model rigidly aligned and scaled to match the image data at the three landmark points is input—for each patient image frame being used. As shown in a block 232 of FIG. 13 and as explained above, the mesh model is used to predict the appearance of the gray scale image in each plane of the images made of the patient's heart. The predicted and observed images are then compared, as indicated in a block 234.

Figure 14:
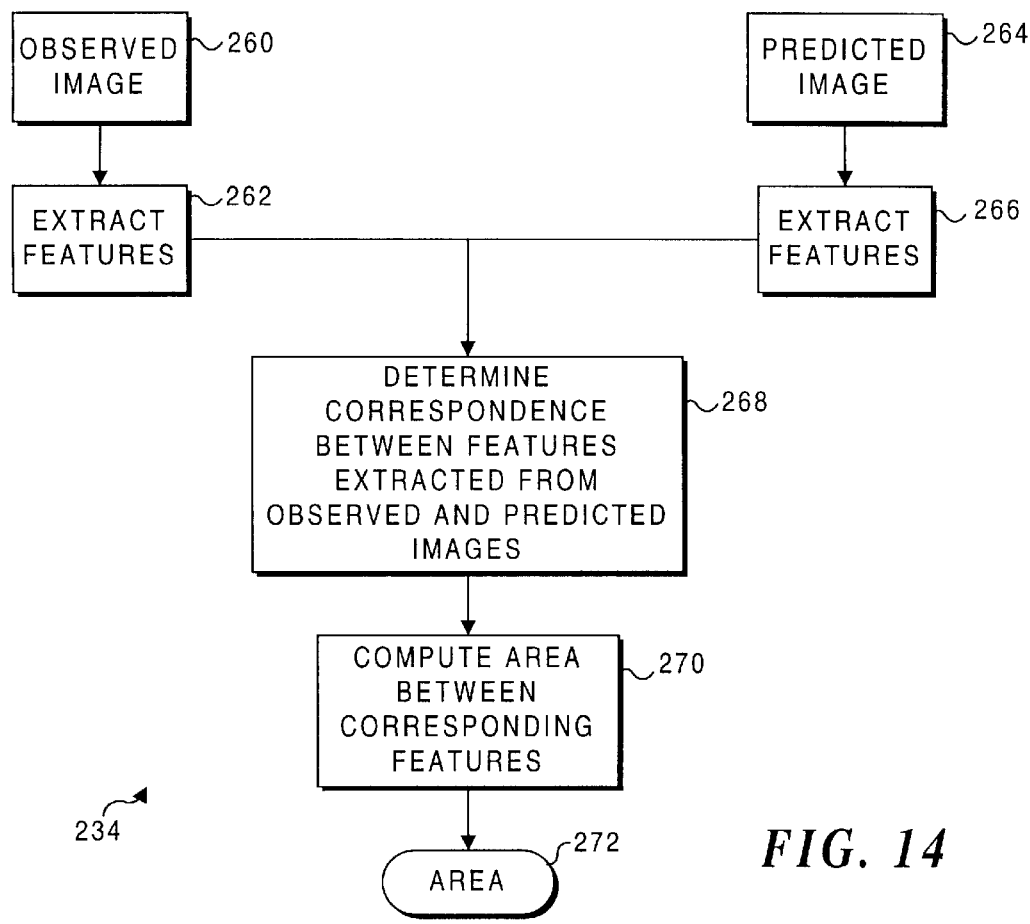
FIG. 14 is a flow chart illustrating the steps for the comparison of the predicted and observed images.

In FIG. 14, details are provided of the step of comparing, which is indicated in block 234. Feature extraction (to locate edge boundaries) is done using an edge operator in a class of facet edge operators. An edge operator locates an edge at a shoulder of a boundary where a contrast change just begins to take place in the image. The shoulder is defined empirically using the manually traced borders in the training data. A gray scale normalization is performed prior to feature extraction, if necessary to adjust for a contrast level.

Blocks 262 and 266 in FIG. 14 respectively provide for extracting features from an observed (patient's) image in a block 260 and from a predicted image in a block 264. In this step, the edge operator is used to obtain polygonal line segments that may be the borders of the left ventricle, as noted above. A block 268 provides for determining a correspondence between features extracted from the observed and predicted images, since they are probably for the same structures in the patient's image and in the predicted image. As a measure of the correspondence, an area (as noted in a block 272) is computed between the corresponding features, as indicated in a block 270.

Figure 15:
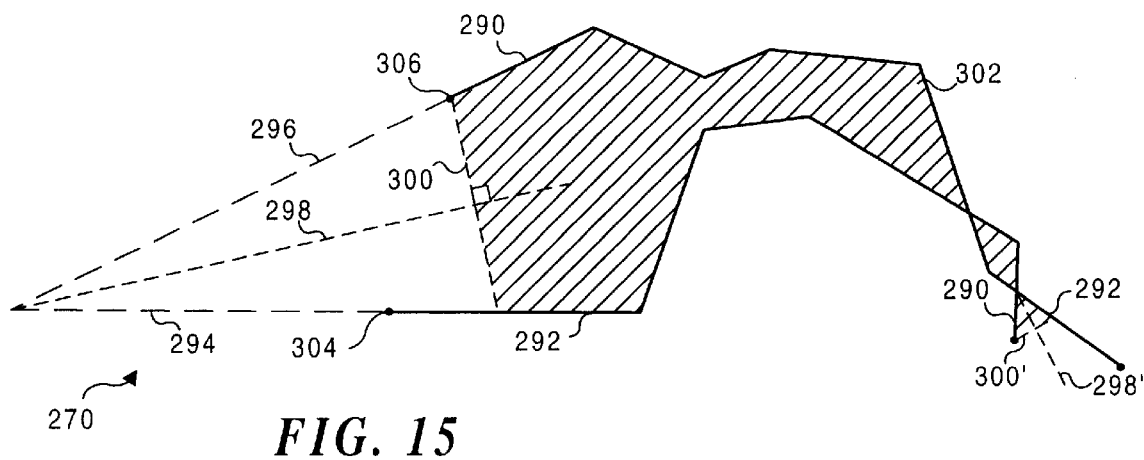
FIG. 15 is a schematic illustration showing how an area is determined between two polygonal line segments that have been extracted from an observed image and its corresponding predicted image.

FIG. 15 provides an exemplary illustration of how an area 302 between two polygonal line segments 290 and 292 is determined. Polygonal line segments 290 and 292 are the edges of features extracted from the observed image produced by imaging the patient's heart and the corresponding predicted image, respectively. At the left side (as seen in the Figure), the pair of polygonal line segments end at points 306 and 304, respectively. A bisector line segment 298 is constructed such that it bisects an angle formed between dash lines 296 and 294, which are produced by extending polygonal line segments 290 and 292, respectively, from their end points. A line 300, which is orthogonal to bisector line segment 298, is then constructed beginning at endpoint 306 of polygonal line segment 290. Similarly, after a line 300' (orthogonal to a bisector line segment 298') is constructed at the ends of the polygonal line segments on the right side of this Figure, area 302 between the line segments representing the two corresponding features is defined, and the size of area 302 can readily be computed.

Referring again to FIG. 13, a block 236 provides for performing a global spatial affine transformation of the ultrasound mesh model. The process of manipulating the mesh model so that the predicted images created from the mesh model more closely match the corresponding images of the patient's heart is achieved by adjusting the control vertices of the mesh model. The first non-rigid adjustment initially implements a global spatial affine transformation of the prototype mesh so that the positions of the three anatomic landmarks in the predicted images match the three anatomic landmark points in the images of the patient's heart that were initially traced (identified) by the user. Subsequent adjustments are made to the position of vertices controlling the shape of the mesh, for example, to force lateral walls of the mesh model to match the corresponding feature boundaries on each image of the patient's heart. Early in the process, only a few control vertices for the abstract mesh of the mesh model may be adjusted to match the key gray scale features in the predicted images with corresponding features in the images of the patient's heart. As the iterations of the optimization bring the predicted images closer to the images patient's heart, additional fine adjustments are made, employing more of the vertices. Throughout this optimization process, the knowledge base of the ventricular shape embodying the archetype shape and covariance matrix is used to constrain the adjustments to ventricular shapes that are anatomically allowable, as well as most probable, given the imaging data for the patient.

To speed up mesh optimization, which is resource intensive, the vertices of the control mesh for the mesh model are preferably divided into subgroups such that each vertex in a subgroup can be adjusted independently, without affecting the area calculation that would be influenced by any other vertex in the same subgroup. The vertices are labeled off line so that no pair of vertices associated with the same triangular facet on the mesh are assigned to the same subgroup. Ensuring independence of vertices within the same subgroup reduces computations in the optimization process, which is a gradient descent optimization requiring partial derivatives of the area with respect to each of the coordinates of the control vertices in the subgroup being adjusted.

The partial derivatives are used to decide the direction in which the control vertices of the subgroup should be adjusted to improve the match between the predicted images and observed images. The extent of the adjustment in the direction defined by the partial derivative is determined using the "golden search" technique. (The golden search technique is described in many references; see, for example, the text by Philip Gill, Walter Murray, and Margaret Wright, "Practical Optimization," Academic Press, New York, 1981.)

A decision block 238 determines if the last adjustment to the control vertices of the mesh model produced predicted images that match the images of the patient's heart with an error that is less than a predefined threshold. In the preferred embodiment, this predefined threshold is 3 $mm^2$, but it should be understood that this threshold value is empirically determined and will likely be changed as further refinements to the invention occur. If the error is less than the predefined threshold, the procedure proceeds to a block 242, since it appears that the predicted images derived from the adjusted mesh model match the images of the patient's heart within an acceptable tolerance. Otherwise, the logic continues with a block 236, which adjusts the mesh model to reduce the area between the corresponding features extracted from the predicted and the observed images.

To measure whether the last adjustment to the control vertices of the mesh model improved the match between features extracted from the predicted images and the observed images of the patient's heart, the mesh model is used to generate a new set of predicted images corresponding to the planes of the patient's image data. The feature extraction, comparison of features between predicted and observed images, and the area assessment are repeated. The adjustments to the shape of the mesh model is constrained by the knowledge base embedded in the mesh model. That is, the archetype shape and covariance matrix reflecting the most probable shape of the LV and the probabilities of variations from the archetype shape require this process to produce a heart-like shape. This result is achieved by applying a penalty function when feature matching suggests a shape that is clinically improbable.

The mesh model is thus adjusted to fit the observed images for the patient's heart in an iterative process, finally yielding a three-dimensional surface that best represents the shape of the patient's heart; the process also ensures that this surface retains the anatomical shape expected of a human heart and that there is a close match between the features in the predicted images arising from the adjusted mesh model and the corresponding features in the observed images. As a further test, a decision block 244 enables the user to determine if the results are acceptable. The border of the left ventricle in any imaging plane can be reviewed and verified by the user by intersecting the three-dimensional surface (endocardial or epicardial) of the adjusted mesh model with the desired plane of the image. If any border is not acceptable to the user, then a decision block 246 determines if the operator wants to manually edit the abstract mesh of the mesh model to achieve a still closer match between the resulting predicted images and the observed images of the patient's heart. In decision block 244, the user can visually inspect the contour of the ventricle that is thus determined for consistency, for example, based upon a comparison of the contour to the observed images.

If the operator wants to manually edit the abstract mesh of the mesh model, the editing process is implemented manually, as indicated in a block 248, and the logic then leads to a block 250, which returns to a block 36 (in FIG. 1). If the user elects not to manually edit the mesh model shape, the program is terminated.

At this point, assuming the portion of the heart being evaluated is the left ventricle, the method will have produced an output comprising three-dimensional meshes representing the endocardial and epicardial surfaces of the left ventricle. These meshes can be used to determine cardiac parameters such as ventricular volume, mass, and function, ejection fraction, wall thickening, etc., as indicated in block 36 of FIG. 1.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A method for delineating a three-dimensional surface of a patient's heart, comprising the steps of.

(a) imaging the patient's heart to produce imaging data that define a plurality of observed images along a corresponding plurality of image planes extending through the patient's heart;

(b) providing a three-dimensional mesh model derived from training data collected by imaging and tracing shapes of a plurality of other hearts;

(c) identifying a plurality of predefined anatomical locations in the observed images of the patient's heart;

(d) rigidly aligning the mesh model with the observed images of the patient's heart, in respect to said predefined anatomical locations;

(e) producing predicted images from the mesh model as rigidly aligned, said predicted images corresponding to the images in the image planes of the imaging data;

(f) optimizing a fit of the predicted images to the observed images of the patient's heart, by repetitively adjusting the mesh model to reduce an error in the fit; and (g) providing an output that defines a three-dimensional endocardial surface and a three-dimensional epicardial surface of the mesh model after said mesh model has been adjusted to optimize the fit in step (f), said output representing the three-dimensional surface of at least a portion of the patient's heart.

2. The method of claim 1, wherein the step of imaging comprises the step of producing ultrasonic images of the patient's heart using an ultrasonic imagining device disposed at known positions and orientations relative to the patient's heart.

3. The method of claim 1, wherein the paliemnit's heart is imaged at a plurality of times during a cardiac cycle, including at an end diastole and at end systole.

4. The method of claim 1, wherein the mesh model is based upon an archetype shape derived from shapes of the plurality of the other hearts of the training data and on a covariance matrix that indicates an extent of variation in three dimensions for each of a plurality of control vertices for the mesh model that permit a shape of the mesh model to be adjusted.

5. The method of claim 1, wherein the step of rigidly aligning comprises the steps of rigidly rotating, translating, and scaling the mesh model as necessary to position and orient the mesh model relative to the observed images in the image planes, so that the predefined anatomical locations in the observed images for the patient's heart are generally matched to corresponding anatomical locations in the predicted images derived from the mesh model.

6. The method of claim 5, wherein intersections of the imaging planes of the patient's heart with the mesh model define the predicted images.

7. The method of claim 1, wherein the step of optimizing comprises the step of reiteratively adjusting said abstract mesh so that features in the predicted images more closely match corresponding features in the observed images of the patient's heart, using control vertices that modify a shape of said mesh.

8. The method of claim 7, wherein the control vertices are divided into subgroups so that control vertices associated with adjusting a common portion of the mesh are not assigned to the same subgroup.

9. The method of claim 1, wherein the step of optimizing includes the step of comparing the predicted images to the observed images of the patient's heart.

10. The method of claim 9, wherein the step of comparing comprises the steps of determining an area between corresponding anatomical features in the predicted images and in the observed images of the patient's heart.

11. The method of claim 10, further comprising the step of generating new predicted images after the fit of the mesh model to the observed images of the patient's heart has been adjusted, said new predicted images being then compared to the observed images of the patient's heart to determine if the fit between the new predicted images and the observed images of the patient's heart is sufficiently optimized.

12. The method of claim 1, further comprising the step of determining if the shape of the three-dimensional surface is clinically probable.

13. The method of claim 1, wherein the three-dimensional surface is of a left ventricle of the patient's heart.

14. The method of claim 1, wherein the three-dimensional surface of at least a portion of the patient's heart is determined for different parts of a cardiac cycle.

15. A method for determining a physiological function of a patient's heart, comprising the steps of:

(a) imaging the patient's heart along a plurality of different image planes at different times during one or more cardiac cycles, producing a plurality of observed images;

(b) determining a three-dimensional shape of the patient's heart for different parts of the cardiac cycle by aligning and fitting a mesh model derived from training data produced by imaging a plurality of other hearts to the observed images of the patient's heart, said three-dimensional shape including at least one of an endocardial surface and an epicardial surface; and (c) evaluating and analyzing a physiological function of the patient's heart based upon contours of said at least one of the endocardial and epicardial surfaces, and changes thereof occurring during a cardiac cycle.

16. The method of claim 15, wherein said at least one of the endocardial and epicardial surfaces are determined at an end diastole and at an end systole of the cardiac cycle.

17. The method of claim 15, further comprising the steps of employing the three-dimensional shape of the patient's heart to determine for at least a portion of the patient's heart, at least one of a volume, a shape, an ejection fraction, a wall motion, and a wall thickening.

18. The method of claim 15, further comprising the step of estimating a border of at least a portion of the patient's heart along a plane by intersecting the three-dimensional shape with the plane.

19. A method for creating a three-dimensional reconstruction of at least a portion of a patient's heart, comprising the steps of:

(a) providing image data of the patient's heart, said image data comprising a plurality of observed images for corresponding image planes;

(b) identifying specific anatomical landmarks within the plurality of observed images;

(c) providing a mesh model that is derived from a set of knowledge base image data for a plurality of other hearts, said set of knowledge base image data including an archetype three-dimensional shape and covariance data for the archetype three-dimensional shape;

(d) initially aligning the mesh model to the plurality of observed images for the patient's heart, by reference to the specific anatomical landmarks;

(e) reiteratively adjusting the mesh model to optimize its fit to the plurality of observed images for the patient's heart, constrained by the archetype three-dimensional shape and the covariance data; and (f) using the mesh model as reiteratively adjusted in step (e) to define the three-dimensional reconstruction of the patient's heart.

20. The method of claim 19, wherein the step of reiteratively adjusting the mesh model comprises the step of modifying a shape of a three-dimensional mesh that is embedded in the mesh model, by adjusting a plurality of control points to change the shape of said mesh.

21. The method of claim 20, wherein the step of reiteratively adjusting comprises the steps of:

(a) determining predicted images from the mesh model after it has been adjusted, said predicted images corresponding to the plurality of images of the patient's heart;

(b) comparing the predicted images to the plurality of the images of the patient's heart, to determine areas between anatomical features in the plurality of observed images and corresponding anatomical features in the predicted images; and (c) adjusting the mesh of the mesh model with the control points to minimize the areas between the anatomical features in the plurality of observed images and the corresponding anatomical features in the plurality of predicted images.

22. The method of claim 21, wherein the predicted images are determined from intersections of planes with the mesh model, where said planes correspond to the image planes through the patient's heart.

23. The method of claim 19, wherein the three-dimensional reconstruction defines at least one of an endocardial surface and an epicardial surface of the patient's heart.

24. The method of claim 19, wherein the three-dimensional reconstruction is one of a left ventricle and a right ventricle of the patient's heart.

25. The method of claim 24, wherein for the left ventricle, the specific anatomical landmarks comprise at least one of an aortic valve, a mitral valve, and a ventricular apex.

26. The method of claim 19, further comprising the step of employing ultrasound to image the patient's heart, to produce the plurality of images comprising the image data.

27. A method for producing a three-dimensional reconstruction of at least a portion of a patient's organ, comprising the steps of:

(a) imaging the organ to produce a plurality of observed images along a corresponding plurality of image planes that extend through the patient's organ;

(b) providing a three-dimensional mesh corresponding to an archetype shape derived from training data collected by imaging and tracing shapes of a plurality of organs in other individuals, said plurality of organs each being of the same type as the patient's organ, said three-dimensional mesh being adjustable in shape;

(c) adjusting the three-dimensional mesh to fit the plurality of images of the patient's organ, producing an adjusted three-dimensional mesh; and (d) producing an output comprising the adjusted three-dimensional mesh, said output reconstructing at least the portion of the patient's organ.

* * * * *

UNITED STATES PATENT AND TRADEMARK OFFICE
CERTIFICATE OF CORRECTION

PATENT NO. : 6,106,466
DATED : August 22, 2000
INVENTOR(S) : Sheehan et al.

It is certified that error appears in the above-identified patent and that said Letters Patent is hereby corrected as shown below:

Column 9,
Line 60, (Equation 2), " $I_t = I_i - I_r = I_i 4Z_2 Z_1 \cos^2 \dfrac{\theta_i}{(Z_2 \cos\theta_i + Z_1 \cos\theta_i)^2}$ "

should read  $-- I_t = I_i - I_r = I_i \dfrac{4Z_2 Z_1 \cos^2 \theta_i}{(Z_2 \cos\theta_i + Z_1 \cos\theta_i)^2} --$ Column 18,
Line 23, "paliemnit's" should read -- patient's --

Signed and Sealed this

Eighth Day of January, 2002

Attest:

JAMES E. ROGAN
*Attesting Officer*  *Director of the United States Patent and Trademark Office*